(12) United States Patent
Hashizume et al.

(10) Patent No.: US 11,237,139 B2
(45) Date of Patent: Feb. 1, 2022

(54) ODOR MEASUREMENT APPARATUS AND ODOR DATA MANAGEMENT APPARATUS

(71) Applicant: AROMA BIT, INC., Tokyo (JP)

(72) Inventors: Kenichi Hashizume, Tokyo (JP); Shunichiro Kuroki, Tokyo (JP)

(73) Assignee: AROMA BIT, INC.

( * ) Notice: Subject to any disclaimer, the term of this patent is extended or adjusted under 35 U.S.C. 154(b) by 240 days.

(21) Appl. No.: 16/366,791

(22) Filed: Mar. 27, 2019

(65) Prior Publication Data

US 2019/0227042 A1 Jul. 25, 2019

Related U.S. Application Data

(63) Continuation of application No. PCT/JP2016/078501, filed on Sep. 27, 2016.

(51) Int. Cl.
| | |
|---|---|
| *G01N 30/74* | (2006.01) |
| *G01N 5/02* | (2006.01) |
| *G01N 27/12* | (2006.01) |
| *G01N 27/407* | (2006.01) |
| *G01N 27/416* | (2006.01) |

(Continued)

(52) U.S. Cl.
CPC ............. *G01N 30/74* (2013.01); *G01N 5/02* (2013.01); *G01N 27/12* (2013.01); *G01N 27/407* (2013.01); *G01N 27/4162* (2013.01); *G01N 29/02* (2013.01); *G01N 2030/025* (2013.01)

(58) Field of Classification Search
None
See application file for complete search history.

(56) References Cited

U.S. PATENT DOCUMENTS 3,538,750 A * 11/1970 Lynnworth .......... G01N 29/228
    374/45
3,877,291 A *  4/1975 Hoppesch .......... G01N 33/4972
    73/23.3

(Continued)

FOREIGN PATENT DOCUMENTS

| JP | 3074494 U | 1/2001 |
|---|---|---|
| JP | 2001-314433 A | 11/2001 |

(Continued)

OTHER PUBLICATIONS

Extended European Search Report for European Patent EP16917645, dated May 22, 2020.

(Continued)

*Primary Examiner* — Daniel S Larkin
(74) *Attorney, Agent, or Firm* — Fresh IP PLC; Clifford D. Hyra; Aubrey Y. Chen

(57) ABSTRACT

An odor measurement apparatus includes an odor sensor detecting an odor and an imaging device having a lens portion, in which an imaging direction of the imaging device and an introduction direction of air when the air is guided to a sensor surface of the odor sensor through an introduction port are substantially the same direction. The odor measurement apparatus detects odor substances contained in air using a sensor when an odor is measured, and measures attribute information of a measurement target or the like of the odor. An odor data management apparatus stores and manages odor data measured by the odor measurement apparatus.

11 Claims, 9 Drawing Sheets

(51) Int. Cl.
*G01N 29/02* (2006.01)
*G01N 29/24* (2006.01)
*G01N 33/00* (2006.01)
*G01N 30/02* (2006.01)

(56) References Cited

U.S. PATENT DOCUMENTS

| | | | | |
|---|---|---|---|---|
| 5,945,069 | A * | 8/1999 | Buehler | G01N 27/126 |
| | | | | 422/90 |
| 6,170,318 | B1 * | 1/2001 | Lewis | G01N 27/126 |
| | | | | 340/632 |
| 8,524,501 | B2 * | 9/2013 | Adams | G01Q 10/045 |
| | | | | 436/22 |
| 9,121,840 | B2 * | 9/2015 | Minvielle | G01N 33/02 |
| 9,645,127 | B2 | 5/2017 | Amin et al. | |
| 10,215,742 | B2 * | 2/2019 | Choi | G01N 33/0009 |
| 2012/0024042 | A1 * | 2/2012 | Vass | G01N 33/0031 |
| | | | | 73/23.34 |
| 2013/0160571 | A1 * | 6/2013 | Williamson | F16L 55/00 |
| | | | | 73/863.41 |
| 2013/0192338 | A1 * | 8/2013 | Mayer | G01N 33/4972 |
| | | | | 73/23.3 |
| 2013/0197384 | A1 * | 8/2013 | Tang | A61B 5/7264 |
| | | | | 600/532 |
| 2013/0244336 | A1 | 9/2013 | Mayer | |
| 2014/0096590 | A1 * | 4/2014 | Amin | H04W 4/029 |
| | | | | 73/23.34 |
| 2014/0134053 | A1 * | 5/2014 | Mayer | G01N 33/0009 |
| | | | | 422/83 |
| 2014/0201182 | A1 | 7/2014 | Amin | |
| 2015/0219608 | A1 | 8/2015 | Choi et al. | |

FOREIGN PATENT DOCUMENTS

| | | |
|---|---|---|
| JP | 2003331369 | 11/2003 |
| JP | 2004-205258 A | 7/2004 |
| JP | 2005-024426 A | 1/2005 |
| JP | 2010025728 A | 2/2010 |
| JP | 2011071908 | 4/2011 |
| JP | 2012-124601 A | 6/2012 |
| JP | 2014085114 | 5/2014 |
| JP | WO 2016/031080 | 3/2016 |
| JP | 2016090460 A | 5/2016 |
| WO | 99/47905 A | 9/1999 |
| WO | WO/2009/157187 | 12/2009 |

OTHER PUBLICATIONS

Japanese Office Action for Japanese Patent JP2018-541761, dated Jun. 2, 2020.
International Search Report dated Nov. 15, 2016.
Hidenao Tanaka et al., "Study On Qcm Gas Sensor For Plume Tracking Robot", IEICE Technical Report, Jul. 30, 2002 (Jul. 30, 2002), vol. 102, No. 255(OEM2002 38-46), pp. 1 to 6.
Kensaku Kashiwagi et al., "Nioi Sensor to Ky ukaku Display 0 Moc hiita Enkaku Nioi Eizo Saigen System no Seino Koj o", Information Processing Society of Japan Symposium Ronbunshu, Mar. 3, 2011 (Mar. 3, 2011), vol. 2011, No. 3, pp. 527 to 530.
Japanese Office Action for Japanese Patent Application 2018-541761, dated May 25, 2021.

* cited by examiner

| Odor Data | Measurement Data | | | | | | | | | Date and Time Data | Image Data | Latitude Data | Longitude Data |
|---|---|---|---|---|---|---|---|---|---|---|---|---|---|
| | i | ii | iii | iv | v | vi | vii | viii | ix | | | | |
| A | Ai | Aii | Aiii | Aiv | Av | Avi | Avii | Aviii | Aix | A1 | A2 | A3 | A4 |
| B | Bi | Bii | Biii | Biv | Bv | Bvi | Bvii | Bviii | Bix | B1 | B2 | B3 | B4 |
| C | Ci | Cii | Ciii | Civ | Cv | Cvi | Cvii | Cviii | Cix | C1 | C2 | C3 | C4 |
| ... | ... | ... | ... | ... | ... | ... | ... | ... | ... | ... | ... | ... | ... |

Fig.9

ODOR MEASUREMENT APPARATUS AND ODOR DATA MANAGEMENT APPARATUS

CROSS-REFERENCE TO RELATED APPLICATION

The present application is a continuation application of PCT International Application No. PCT/JP2016/078501, filed Sep. 27, 2016. The contents of this application are incorporated herein by reference in their entirety.

BACKGROUND

Field

The present invention relates to an odor measurement apparatus and an odor data management apparatus. Specifically, the invention relates to an odor measurement apparatus that measures an odor of air and an odor data management apparatus that manages odor data as a measurement result thereof.

Description of the Related Art

There has been a known sensor including a crystal oscillator that specifically adsorbs an odor substance in air to measure the odor of the air (see Patent Document 1: JP 5-187986 A).

However, merely by measuring an odor of the air using a sensor and saving a measurement result thereof, it is impossible to grasp the attribute information of the odor, such as which odor has been measured (a measurement target of the odor), where the odor has been measured (measurement location), and in which environment the odor has been measured (measurement environment). In addition, to collect these pieces of attribute information, measurers need to measure and record the measurement target, the measurement location, the measurement environment, etc. of the odor each time the odor is measured.

The invention has been made in view of the above circumstances, and an illustrative object of the invention is to provide an odor measurement apparatus and an odor management apparatus that manages a measurement result thereof, the odor measurement apparatus detecting an odor substance contained in air using a sensor when an odor is measured and measuring attribute information, such as measurement target of the odor.

SUMMARY

To solve the above-mentioned problems, the invention has the following configurations.

(1) An odor measurement apparatus including an odor sensor detecting an odor, and an imaging device having a lens portion, in which an imaging direction of the imaging device and an introduction direction of air when the air is guided to a sensor surface of the odor sensor through an introduction port are substantially the same direction.

Since the imaging direction by the imaging device and the air introduction direction are substantially the same direction, it is possible to detect an odor dispersed in air from a measurement target of the odor using the odor sensor, and to capture the measurement target of the odor using the imaging device without moving the odor measurement apparatus. In addition, measurement and imaging of the odor can be performed at the same time or through a sequence of operations.

In the invention, the "odor" can be acquired by a human or living things including the human as olfactory information and corresponds to a concept including a molecular simple substance or a group of molecules made of different molecules gathered with respective concentrations.

In the invention, the molecular simple substance or the group of molecules made of different molecules gathered with respective concentrations included in the odor is referred to as an "odor substance". However, in a broad sense, the odor substance may broadly mean a substance which can be adsorbed on a substance adsorption membrane, which will be described below. That is, since the "odor" contains a plurality of odor substances responsible for the odor in many cases, and a substance not recognized as the odor substance or an unknown odor substance may be present, a substance generally not regarded as an odor causing substance may be contained.

(2) It is preferable that the odor sensor includes a plurality of sensor elements, each having a substance adsorption membrane which adsorbs odor substances in the air and a detector which detects an adsorption state of the odor substances to the substance adsorption membrane, and an adsorption characteristic of the odor substances to the substance adsorption membrane is different for each of the plurality of sensor elements.

Since the odor sensor includes the plurality of sensor elements, each having the substance adsorption membrane and the detector, and the adsorption characteristic of the odor substance to the substance adsorption membrane is different for each of the sensor elements, it is possible to obtain a measurement result of the odor by the odor sensor as measurement data of an adsorption amount of the odor substance different for each substance adsorption membrane. In this way, it is possible to evaluate the odor as a set (pattern) of measurement data.

(3) It is preferable that the odor measurement apparatus further includes a housing including the odor sensor and the imaging device therein, in which the lens portion of the imaging device and the introduction port are disposed on a predetermined surface corresponding to a surface on the same side in the housing.

When the lens portion and the introduction port of the imaging device are disposed on the predetermined surface corresponding to the surface on the same side in the housing, it is possible to detect an odor dispersed in the air from a measurement target of the odor using the odor sensor, and to capture the measurement target of the odor using the imaging device without moving the odor measurement apparatus. In addition, measurement and imaging of the odor can be performed at the same time or through a sequence of operations.

(4) It is preferable that a ventilation opening is formed on another surface different from the predetermined surface in the housing in the odor measurement apparatus.

When the ventilation opening is formed on another surface different from the predetermined surface in the odor measurement apparatus, it is possible to ventilate air located in the vicinity of the sensor surface of the odor sensor. As a result, it is possible to accelerate desorption of the odor substance adsorbed on the substance adsorption membrane. In this way, by ventilating the air located in the vicinity of the sensor surface with air in an atmosphere, it is possible to reset the odor sensor to an initial state or to adjust a baseline (standard) to an odor level of the air in the atmosphere in preparation for subsequent measurement.

(5) It is preferable that an opening/closing device capable of opening and closing the introduction port is arranged in the odor measurement apparatus.

When the opening/closing device capable of opening and closing the introduction port is arranged, it is possible to more prominently measure the odor of the measurement target. In more detail, when the odor measurement apparatus is moved to the vicinity of the measurement target in a state in which the opening/closing device is closed, and the odor is measured by opening the opening/closing device in a state in which measurement is ready, a difference in odor (a difference in composition of odor substances) becomes large between before and after opening and closing, and a characteristic of the measurement target becomes more prominent in measurement data (odor data) of the odor of the measurement target.

In addition, when the air located in the vicinity of the sensor surface is ventilated using the ventilation opening in the state in which the opening/closing device is closed, it is possible to prevent entry of the odor substance from the introduction port, and to more favorably adjust the baseline (standard).

(6) It is preferable that the odor measurement apparatus further includes a fan controlling introduction of air from the introduction port to the sensor surface.

When the odor measurement apparatus includes a fan controlling introduction of air from the introduction port, it is possible to more actively introduce the odor substance dispersed from the measurement target to the sensor surface of the odor sensor.

(7) It is preferable that the odor measurement apparatus further includes an attribute data acquisition device including at least one of a global positioning system (GPS) device, a thermo-hygrometer, a barometer, and an illuminometer.

When the odor measurement apparatus further includes an attribute data acquisition device, such as a GPS device, a thermo-hygrometer, a barometer, or an illuminometer in addition to the imaging device, it is possible to acquire attribute data, such as location information, air temperature/humidity information, air pressure information, or illuminance information stored in the storage device in association with each other together with the odor data and the image data. In this way, the attribute information of the odor data is enriched, and the odor data can be classified, organized, and managed in more detail.

(8) It is preferable that the odor measurement apparatus further includes a communication device transmitting odor data measured by the odor sensor and image data generated by the imaging device.

When the odor measurement apparatus further includes the communication device, it is possible to transmit the odor data and the image data from the odor measurement apparatus to a server, or the like. Naturally, it is possible to transmit the attribute data, such as the location information, the air temperature/humidity information, the air pressure information, or the illuminance information to the server, or the like. In this way, it is possible to manage the odor data, the image data and other attribute information in the server, or the like in addition to the odor measurement apparatus.

(9) An odor data management apparatus including receiving means receiving the odor data and the image data transmitted from the odor measurement apparatus, and storing means storing the received odor data and image data in association with each other.

The odor data management apparatus can receive, store, and manage the odor data and the image data transmitted from the odor measurement apparatus by including the receiving means receiving the odor data and the image data, and the storing means storing the received odor data and image data in association with each other. Naturally, it is possible to receive, store, and manage the attribute data as mentioned above, such as the location information, the air temperature/humidity information, the air pressure information, or the illuminance information.

(10) It is preferable that the odor data management apparatus further includes extracting means extracting odor data approximate to specific odor data from a plurality of sets of odor data stored in the storing means, and returning means returning image data associated with odor data extracted by the extracting means as a search result.

Since the odor data management apparatus includes the extracting means extracting odor data approximate to specific odor data from a plurality of sets of odor data stored in the storing means, and the returning means returning image data associated with the extracted odor data as a search result, it is possible to obtain image data with regard to an odor approximate to an odor assigning a specific odor data by searching for the specific odor data. That is, when a specific odor is searched for, it is possible to obtain image data related to an odor approximate to the specific odor as a search result. In this way, it is possible to obtain image data of a measurement target at the time of measuring an odor approximate to a searched specific odor.

Further objects and other features of the invention will become apparent by preferred embodiments described below with reference to the accompanying drawings.

According to the invention, it is possible to provide an odor measurement apparatus and an odor data management apparatus that manages a measurement result thereof, the odor measurement apparatus detecting an odor substance contained in air using a sensor when an odor is measured and measuring attribute information, such as measurement target of the odor.

BRIEF DESCRIPTION OF THE DRAWINGS

FIG. 9 is a database configuration diagram schematically illustrating an odor data management database stored in a storage device 62 of the odor data management apparatus 60 according to the second embodiment.

DETAILED DESCRIPTION

First Embodiment

Figure 1:
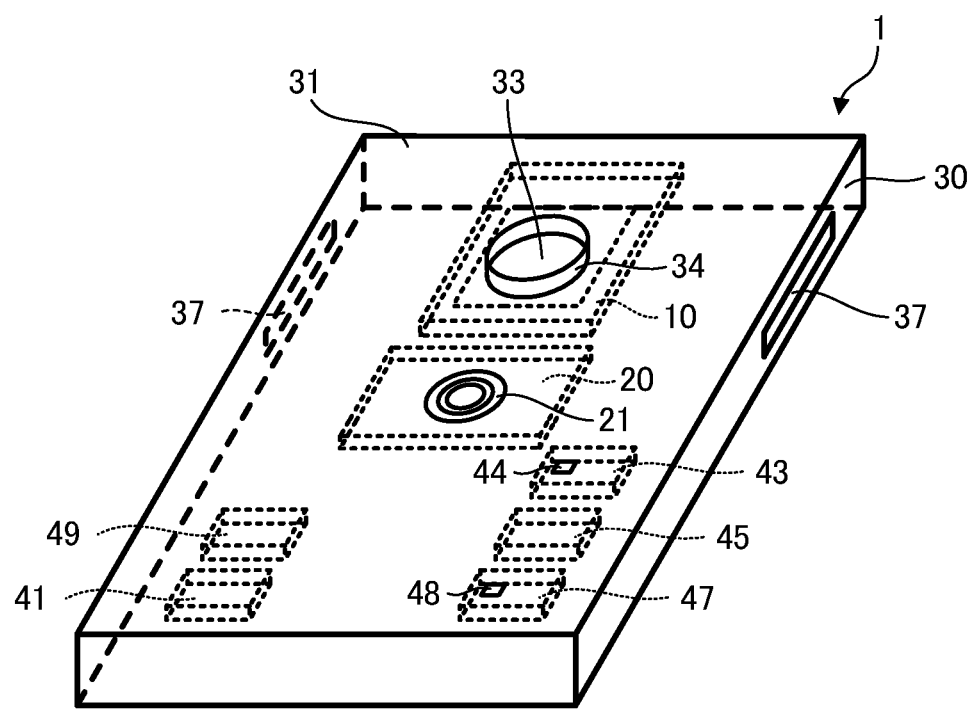
FIG. 1 is a perspective view schematically illustrating an odor measurement apparatus 1 according to the first embodiment.
Figure 2:
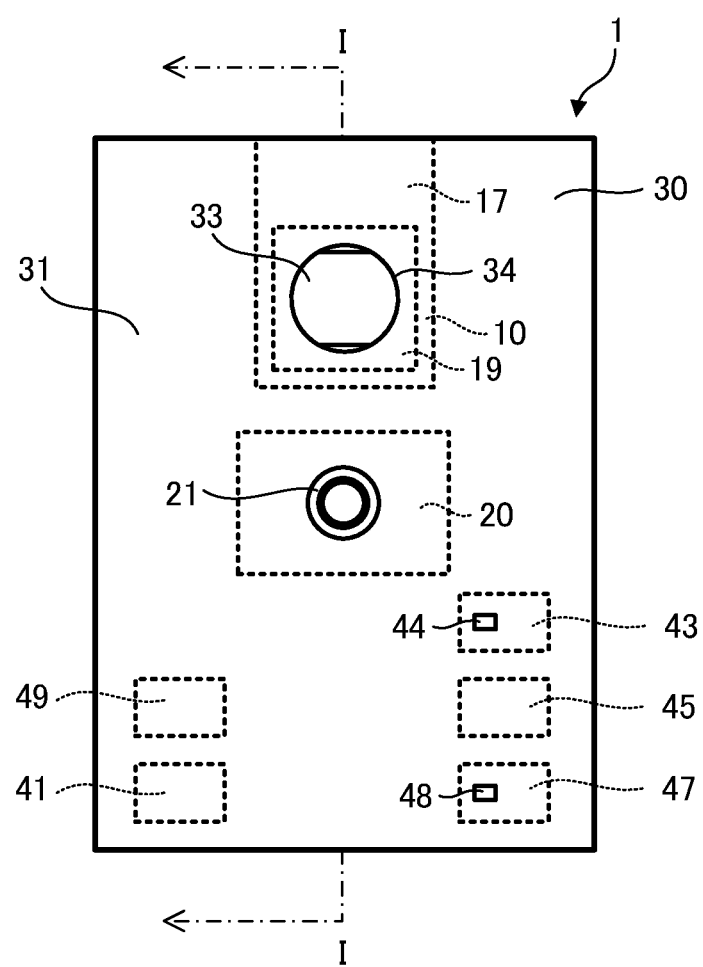
FIG. 2 is a plan view schematically illustrating the odor measurement apparatus 1 according to the first embodiment.
Figure 3:
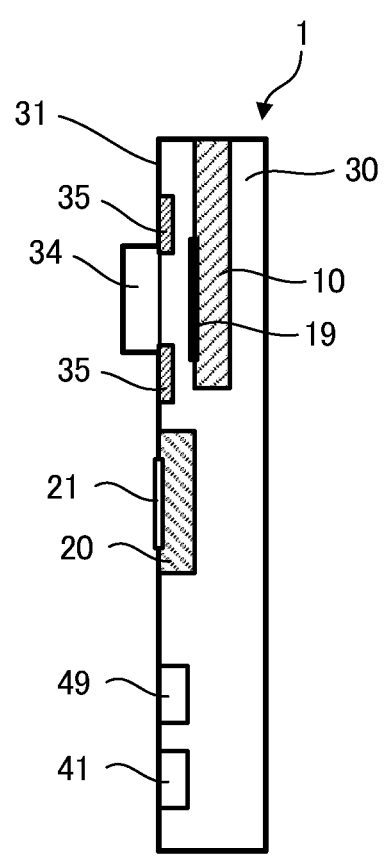
FIG. 3 is a cross-sectional view schematically illustrating the I-I cross-section of FIG. 2.

Hereinafter, an odor measurement apparatus 1 according to the first embodiment will be described with reference to the drawings. FIG. 1 is a perspective view schematically illustrating the odor measurement apparatus 1 according to the first embodiment. FIG. 2 is a plan view schematically illustrating the odor measurement apparatus 1 according to the first embodiment. FIG. 3 is a cross-sectional view schematically illustrating the I-I cross-section of FIG. 2.

The odor measurement apparatus 1 according to the first embodiment includes a housing 30 having a predetermined surface 31. The housing 30 includes an odor sensor 10 therein and an imaging device 20 therein. As illustrated in FIG. 1, the housing 30 has a plate-like shape in which areas of the predetermined surface 31 and the surface on its opposite side are larger. Here, the predetermined surface 31 corresponds to a surface on the same side in the housing 30. The predetermined surface 31 may be a surface positioned on the same side of the housing 30 and may have unevenness or steps. In addition, the predetermined surface 31 may not correspond to a single plane and may be formed of a plurality of surfaces. In FIG. 1, the predetermined surface 31 is a single plane. Further, the surface faces upward in the perspective view of FIG. 1 and faces a nearer side of the plane of the paper in the plan view of FIG. 2.

Figure 6:
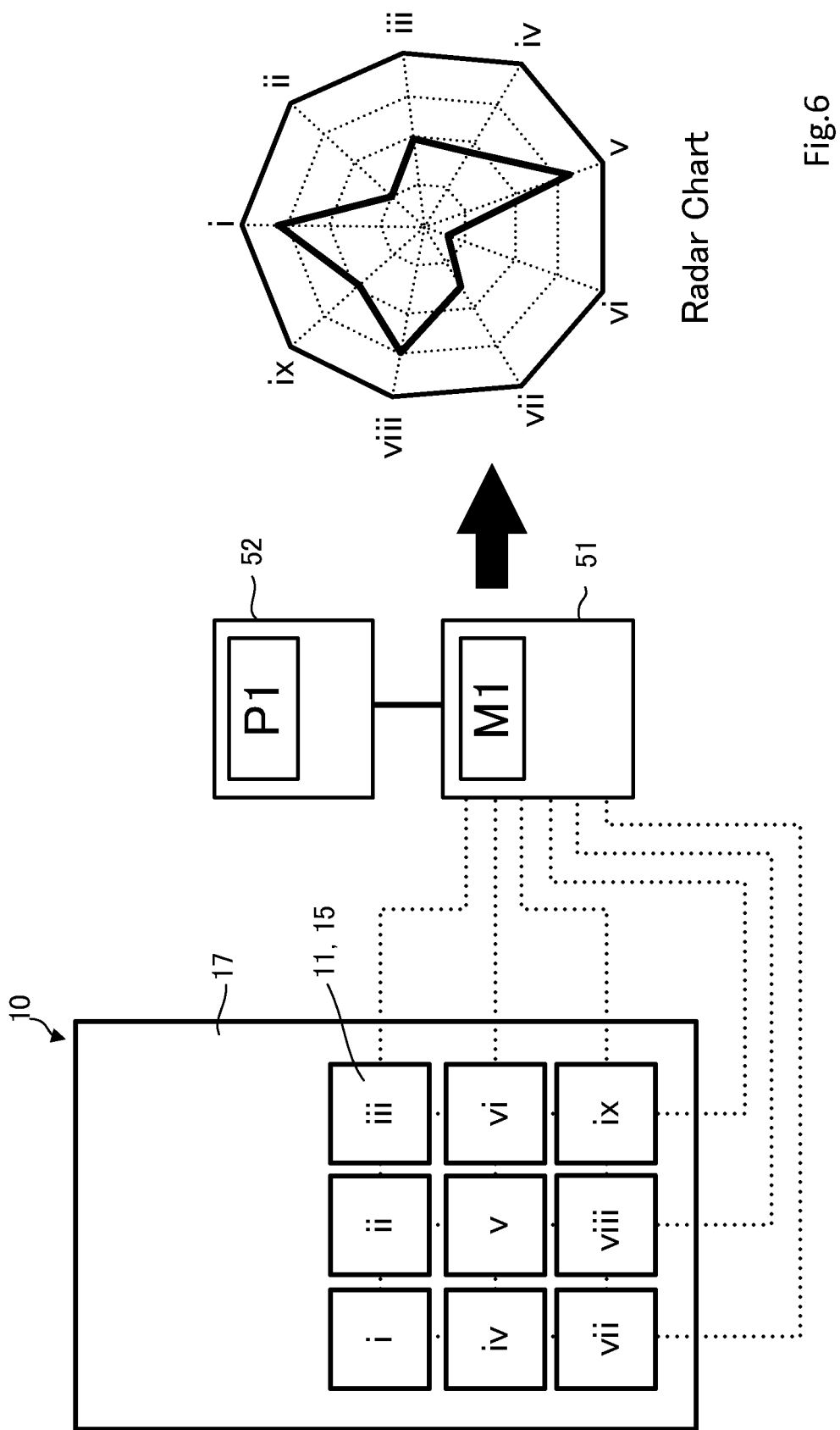
FIG. 6 is an explanatory diagram schematically illustrating an internal configuration of the odor measurement apparatus 1 according to the first embodiment.

The odor measurement apparatus 1 includes an arithmetic processing device 51 (CPU) and a storage device 52 (memory) therein, as shown in FIG. 6. The odor sensor 10 and the imaging device 20 described above are connected to the arithmetic processing device 51, and various sensors described below are also connected thereto. The arithmetic processing device 51 can control the odor sensor 10, the imaging device 20, and the other various sensors. Incidentally, in the figure, wiring connecting the arithmetic processing device 51 and various devices or sensors is not illustrated.

The odor measurement apparatus 1 may share a housing 30 of a portable information terminal, such as a smartphone or a tablet terminal as the housing 30. That is, the odor measurement apparatus 1 can be incorporated in the portable information terminal, such as the smartphone or the tablet terminal. In such case, the predetermined surface 31 can be the surface on an opposite side from a surface on which a display unit of the smartphone or the tablet terminal is arranged. Incidentally, devices, sensors, and the like originally included in the portable information terminal, such as arithmetic processing device 51, storage device 52, imaging device 20, or GPS device 41, can be shared between the portable information terminal and the odor measurement apparatus 1.

An introduction port 33 for introducing air to a sensor surface 19 of the odor sensor 10 is formed on the predetermined surface 31. A guide portion 34 protruding outward from the housing 30 is provided on the introduction port 33 to surround a periphery thereof. The odor sensor 10 is arranged inside the housing 30 and is indicated by a dotted line in FIG. 1. A specific configuration of the odor sensor 10 will be described later.

A lens portion 21 of the imaging device 20 is arranged on the predetermined surface 31. The imaging device 20 is indicated by a dotted line in FIG. 1. A specific configuration of the imaging device 20 will be described later.

A direction (introduction direction) in which air is introduced through the introduction port 33 and an imaging direction of the imaging device 20 are substantially in the same direction. That the air introduction direction and the imaging direction are substantially in the same direction means that the introduction port 33 is formed so that the air introduction direction is substantially in the same direction as the imaging direction. In addition, that the air introduction direction and the imaging direction are substantially in the same direction means that an incident direction in which light arriving at the imaging device 20 through the lens portion 21 enters the lens portion 21 is substantially in the same direction as the air introduction direction. Incidentally, the incident direction in which light arriving at the imaging device 20 enters the lens portion 21 has a certain angular range within an imaging range, and the imaging direction includes the angular range of the incident direction. For this reason, a case in which the air introduction direction and the imaging direction are not strictly in the same direction can be included, and thus an expression "substantially in the same direction" is used.

As illustrated in FIG. 2 and FIG. 3, a shutter 35 as an opening/closing device capable of opening and closing the introduction port 33 is disposed in the housing 30. Incidentally, in FIG. 1, illustration of the shutter 35 is omitted. The shutter 35 has two flat plates disposed to face each other and is configured to seal the introduction port 33 by sliding and moving the two flat plates close to each other and making contact. The shutter 35 may be a single flat plate having a size capable of sealing the introduction port 33 configured to slide and move. The configuration of the shutter 35 is not limited thereto, and any known configuration can be appropriately employed.

A ventilation opening 37 for ventilating air in the vicinity of the sensor surface 19 of the odor sensor 10 is formed in the housing 30 on a surface different from the predetermined surface 31. In the perspective view of FIG. 1, one ventilation opening 37 is formed on each of right and left surfaces.

As illustrated in FIG. 3, the odor measurement apparatus 1 includes a fan capable of controlling introduction of air from the introduction port 33 to the sensor surface 19 of the odor sensor 10 inside the housing 30. By rotating this fan, it is possible to more forcibly introduce air containing an odor substance of a measurement target from the introduction port 33 to the sensor surface 19 of the odor sensor 10. Incidentally, when the fan is rotated in a reverse direction, air located in the vicinity of the sensor surface 19 can be caused to flow out from the introduction port 33 or the ventilation opening 37.

In the odor measurement apparatus 1, a GPS device 41, a thermo-hygrometer 43, a barometer 45, an illuminometer 47, and a communication device 49 are arranged inside the housing 30. In the odor measurement apparatus 1, various devices other than these devices may be arranged.

The GPS device 41 is a device for specifying a position of the odor measurement apparatus 1 using a global positioning system (GPS), and can output latitude data and longitude data of the odor measurement apparatus 1 at the time of odor measurement. The GPS device 41 need not be exposed to the outside on the surface of the housing 30 of the odor measurement apparatus 1 as long as the GPS device 41 can receive radio waves from a GPS satellite.

Figure 4:
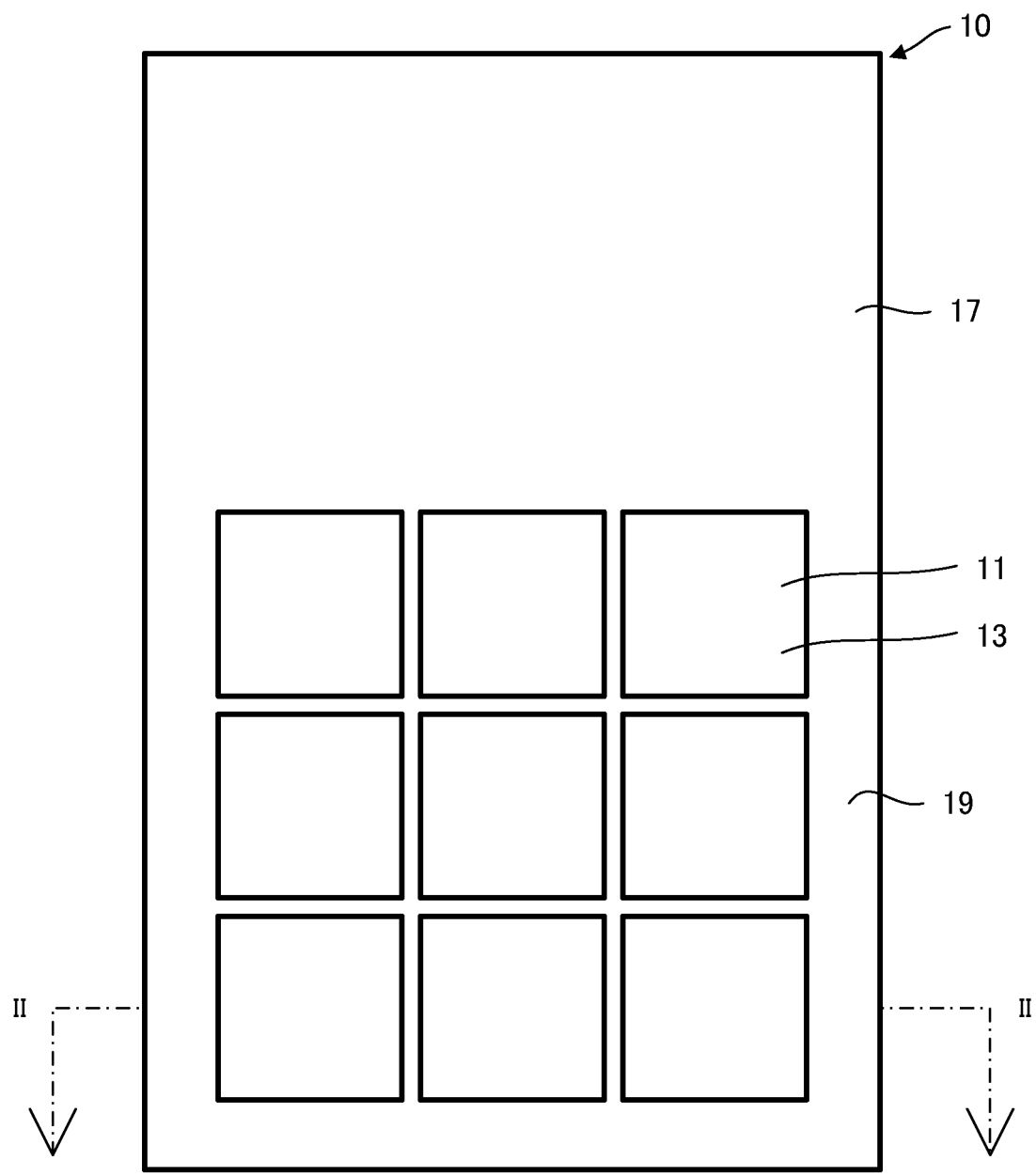
FIG. 4 is a plan view schematically illustrating an odor sensor 10 in the first embodiment.

The thermo-hygrometer 43 is a device for measuring an air temperature and humidity of air in the vicinity of the odor measurement apparatus 1 at the time of odor measurement, and can output air temperature data and humidity data thereof. It is preferable that at least the measuring portion 44 of the thermo-hygrometer 43 is exposed to the outside on the surface of the housing 30 of the odor measurement apparatus 1. When the air temperature and humidity at the time of odor measurement are measured by the thermo-hygrometer 43 and stored in the storage device 52 in association with odor data, it is possible to make the odor data more useful. For example, in a case in which an adsorption characteristic of an odor substance with respect to a substance adsorption membrane 13, as shown in FIG. 4, changes due to an influence of the air temperature or humidity, it is possible to more appropriately evaluate the odor data by grasping the condition of the air temperature and humidity at the time of odor measurement.

The barometer 45 is a device for measuring an air pressure in the vicinity of the odor measurement apparatus 1 at the time of odor measurement, and can output air pressure data thereof. When the air pressure at the time of odor measurement is measured by the barometer 45 and stored in the storage device 52 in association with the odor data, it is possible to make the odor data more useful. For example, in a case in which an adsorption characteristic of the odor substance with respect to the substance adsorption membrane 13 changes due to an influence of the air pressure, it is possible to more appropriately evaluate the odor data by grasping the condition of the air pressure at the time of odor measurement.

The illuminometer 47 is a device for measuring illuminance (light amount) in the vicinity of the odor measurement apparatus 1 at the time of odor measurement, and can output illuminance (light amount) data thereof. It is preferable that at least a measuring portion 48 of the illuminometer 47 is exposed to the outside on the surface of the housing 30 of the odor measurement apparatus 1. In particular, it is preferable that the measuring portion 48 of the illuminometer 47 is exposed to the outside on the predetermined surface 31. When the illuminance (light amount) at the time of odor measurement is measured by the illuminometer 47 and stored in the storage device 52 in association with the odor data, it is possible to make the odor data more useful. By grasping the condition of the illuminance (light amount), image data can be corrected so that an imaging object is more easily recognized.

The communication device 49 is a device capable of transmitting various data generated by various sensors or devices provided in the odor measurement apparatus 1. For example, various data can be transmitted to a server terminal, and these various data can be stored and managed in a storage device 52 of the server terminal.

Examples of the various data include the odor data generated by the odor sensor 10, the latitude data and the longitude data generated by the GPS device 41, the air temperature data and the humidity data generated by the thermo-hygrometer 43, the air pressure data generated by the barometer 45, and the illuminance (light amount) data generated by the illuminometer 47. As the various data, it is possible to include date and time data in which the date and the time at which the odor is measured are recorded. The date and time data can be generated by arbitrary means capable of recording the date and time, such as a date and time recording device mounted on the odor measurement apparatus 1.

<Odor Sensor 10>

Figure 5:
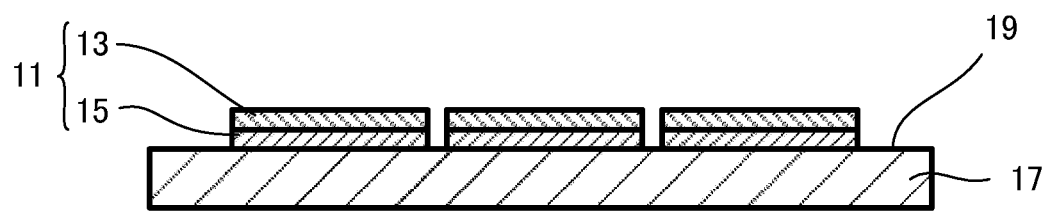
FIG. 5 is a cross-sectional view schematically illustrating the II-II cross-section of FIG. 4.

FIG. 4 is a plan view schematically illustrating the odor sensor 10 in the first embodiment. FIG. 5 is a cross-sectional view schematically illustrating the II-II cross-section of FIG. 4. The odor sensor 10 includes a plurality of sensor elements 11. Each of the sensor elements 11 includes the substance adsorption membrane 13 that adsorbs the odor substance and a detector 15 that detects an adsorption state of the odor substance with respect to the substance adsorption membrane 13.

As illustrated in FIG. 5, the sensor element 11 includes the detector 15 and the substance adsorption membrane 13 provided on the surface of the detector 15. It is preferable that the substance adsorption membrane 13 covers the entire surface of the detector 15. That is, the size of the detector 15 is preferably the same as the formation range of the substance adsorption membrane 13, or smaller than the formation range of the substance adsorption membrane 13. Incidentally, a plurality of detectors 15 may be provided within the formation range of one substance adsorption membrane 13.

The plurality of sensor elements 11 is arranged on a sensor substrate 17 and aligned in a lattice pattern of three rows and three columns as illustrated in FIG. 4. In this instance, substance adsorption membranes 13 of adjacent sensor elements 11 are not in contact with each other or are insulated. It should be noted that the sensor elements 11 may not be aligned on the sensor substrate 17 and may be randomly arranged or aligned in a form other than three rows and three columns.

In the plurality of sensor elements 11 arranged on the sensor substrate 17, properties of the respective substance adsorption membranes 13 are different from each other. Specifically, it is preferable that all the plurality of sensor elements 11 have substance adsorption membranes 13 of different compositions, and that substance adsorption membranes 13 of the same property do not exist. Here, the property of the substance adsorption membrane 13 can be referred to as the adsorption characteristic of the odor substance with respect to the substance adsorption membrane 13. That is, one same odor substance (or an aggregate thereof) can exhibit different adsorption characteristics if the substance adsorption membrane 13 has a different property. In FIG. 4 and FIG. 5, for the sake of convenience, all the substance adsorption membranes 13 are illustrated in the same manner. However, in practice, properties thereof are different from each other.

As a material of the substance adsorption membrane 13, it is possible to use a thin film formed of a π electron conjugated polymer. This thin film can contain at least one of an inorganic acid, an organic acid, or an ionic liquid as a dopant. By changing the type or content of the dopant, it is possible to change the property of the substance adsorption membrane 13.

Examples of the π electron conjugated polymer preferably include, but are not limited to, a polymer having the π electron conjugated polymer as a skeleton, such as polypyrrole and a derivative thereof, polyaniline and a derivative thereof, polythiophene and a derivative thereof, polyacetylene and a derivative thereof, or polyazulene and a derivative thereof.

In a case in which the π electron conjugated polymer is in an oxidized state and the skeleton polymer itself is a cation, conductivity can be developed by containing an anion as a dopant. Incidentally, in the invention, a neutral π electron conjugated polymer not containing a dopant can be adopted as the substance adsorption membrane 13.

Specific examples of the dopant can include inorganic ions, such as chlorine ion, chlorine oxide ion, bromine ion, sulfate ion, nitrate ion, and borate ion, organic acid anions, such as alkylsulfonic acid, benzenesulfonic acid, and carboxylic acid, and polymer acid anions, such as polyacrylic acid and polystyrene sulfonic acid.

In addition, it is possible to use a method of performing chemical equilibrium doping by allowing salt, such as table salt, or an ionic compound containing both a cation and an anion, such as an ionic liquid, to coexist with the neutral π electron conjugated polymer.

In a case in which a state in which one dopant unit (ion) enters per two repeating units included in the π electron conjugated polymer is set to 1, the content of the dopant in the π electron conjugated polymer may be adjusted in a range of 0.01 to 5, preferably in a range of 0.1 to 2. When the content of the dopant is set to be greater than or equal to the minimum value of this range, it is possible to inhibit disappearance of the characteristic of the substance adsorption membrane 13. In addition, when the content of the dopant is set to be less than or equal to the maximum value of this range, it is possible to inhibit a decrease in effect of the adsorption characteristic of the π electron conjugated polymer itself, which makes it difficult to produce the substance adsorption membrane 13 having a desirable adsorption characteristic. In addition, it is possible to inhibit a significant decrease in durability of the substance adsorption membrane 13 due to the dopant, which is a low molecular weight substance, when predominant in the membrane. Therefore, by setting the content of the dopant in the above-mentioned range, it is possible to suitably maintain detection sensitivity of the odor substance.

In the plurality of sensor elements 11, different types of π electron conjugated polymers can be used to vary the respective adsorption characteristics of the substance adsorption membranes 13. In addition, respective adsorption characteristics may be developed by changing the type or the content of the dopant while using the same kind of π electron conjugated polymer. For example, hydrophobic/hydrophilic properties of the substance adsorption membrane 13 can be changed by changing the type of the π electron conjugated polymer, the type and the content of the dopant, etc.

A thickness of the substance adsorption membrane 13 can be appropriately selected according to the characteristic of the odor substance to be adsorbed. For example, the thickness of the substance adsorption membrane 13 can be in a range of 10 nm to 10 μm, preferably 50 nm to 800 nm. When the thickness of the substance adsorption membrane 13 is less than 10 nm, sufficient sensitivity may not be obtained in some cases. In addition, when the thickness of the substance adsorption membrane 13 exceeds 10 μm, an upper limit of the weight detectable by the detector 15 may be exceeded.

The detector 15 has a function as a signal converter (transducer) which measures a change in physical, chemical, or electrical characteristic of the substance adsorption membrane 13 due to the odor substance adsorbed on the surface of the substance adsorption membrane 13 and outputs measurement data thereof as, for example, an electric signal. That is, the detector 15 detects an adsorption state of the odor substance on the surface of the substance adsorption membrane 13. Examples of the signal output as the measurement data by the detector 15 include physical information, such as an electric signal, light emission, a change in electric resistance, or a change in vibration frequency.

The detector 15 is not particularly limited as long as the detector 15 is a sensor which measures the change in physical, chemical, or electrical characteristic of the substance adsorption membrane 13, and various sensors can be appropriately used. Specific examples of the detector 15 include a crystal oscillator sensor (QCM), a surface elastic wave sensor, a field effect transistor (FET) sensor, a charge coupled device sensor, an MOS field effect transistor sensor, a metal oxide semiconductor sensor, an organic conductive polymer sensor, an electrochemical sensor.

Incidentally, in the case of using the crystal oscillator sensor as the detector 15, although not illustrated, as an excitation electrode, electrodes may be provided on both sides of the crystal oscillator or a separated electrode may be provided on one side to detect a high Q value. In addition, the excitation electrode may be provided on the sensor substrate 17 side of the crystal oscillator with the sensor substrate 17 interposed therebetween. The excitation electrode can be formed of an arbitrary conductive material. Specific examples of the material of the excitation electrode include inorganic materials, such as gold, silver, platinum, chromium, titanium, aluminum, nickel, nickel alloy, silicon, carbon, and carbon nanotube, and organic materials, such as conductive polymers, such as polypyrrole and polyaniline.

As illustrated in FIG. 5, the detector 15 can have a flat-plate shape. As illustrated in FIG. 5, a shape of the flat plate of the flat-plate shape can be quadrilateral or square. However, the shape can be of various shapes, such as a circle or an ellipse. Further, the shape of the detector 15 is not limited to the flat plate shape. A thickness thereof may be altered, and a concave portion or a convex portion may be formed.

In a case in which the detector 15 uses an oscillator as the crystal oscillator sensor described above, it is possible to reduce the influence (crosstalk) received from another oscillator coexisting on the same sensor substrate 17 by changing resonance frequencies of respective oscillators in the plurality of sensor elements 11. It is possible to arbitrarily design the resonance frequencies so that the respective oscillators on the same sensor substrate 17 exhibit different sensitivities with respect to a certain frequency. The resonance frequency can be changed, for example, by adjusting the thickness of the oscillator or the substance adsorption membrane 13.

As the sensor substrate 17, it is possible to use a silicon substrate, a substrate made of quartz crystal, a printed wiring substrate, a ceramic substrate, a resin substrate, etc. In addition, the substrate is a multilayer wiring substrate, such as an interposer substrate, and an excitation electrode for oscillating the quartz substrate, mounting wirings, and an electrode for energizing are disposed at arbitrary positions.

By adopting the configuration as described above, it is possible to obtain the odor sensor 10 including the plurality of sensor elements 11 having the substance adsorption membranes 13 whose adsorption characteristics of the odor substance are different from each other. As a result, in a case in which an odor of air containing a certain odor substance or a composition thereof is measured by the odor sensor 10, the odor substance or the composition thereof comes into contact with the substance adsorption membrane 13 of each sensor element 11 in the same manner. However, the odor substance is adsorbed to the respective substance adsorption membranes 13 in different modes. That is, an adsorption amount of the odor substance is different between the respective substance adsorption membranes 13. For this reason, a detection result of the detector 15 is different between the respective sensor elements 11. Therefore, pieces of measurement data by the detector 15 corresponding to the number of sensor elements 11 (substance adsorption membranes 13) included in the odor sensor 10 are generated for the certain odor substance or the composition thereof.

A set of measurement data (hereinafter referred to as odor data) generated by the odor sensor 10 by measuring the certain odor substance or the composition thereof is usually specific (unique) to a specific odor substance or a composition of the odor substance. For this reason, by measuring the odor data using the odor sensor 10, it is possible to identify the odor as an odor substance alone or as a composition (mixture) of odor substances.

Next, a configuration of an odor data acquiring means for acquiring odor data using the odor sensor 10 will be described. FIG. 6 is an explanatory diagram schematically illustrating an internal configuration of the odor measurement apparatus 1 according to the first embodiment. Odor acquiring means M1 is stored in the storage device 52 as program P1, and the odor sensor 10 can be caused to function as the odor acquiring means M1 by causing the arithmetic processing device 51 to execute the program. Incidentally, acquisition of odor data may be executed by another configuration without aid of the arithmetic processing device 51.

The arithmetic processing device 51 is connected to each detector 15 of the odor sensor 10 to acquire measurement data measured by each detector 15 wherein an odor substance is adsorbed to each substance adsorption membrane 13. At this time, each piece of measurement data is stored in the storage device 52 in association with a position of each detector 15 on the odor sensor 10, that is, arrangement information of the detector 15. In other words, in a case in which the respective detectors 15 in the odor sensor 10 have the same configuration, each piece of measurement data is stored in association with each substance adsorption membrane 13 of the odor sensor 10 on a one-to-one basis. Specifically, as illustrated in FIG. 6, measurement data is measured for each of detectors i to ix. Further, for example, respective pieces of the measurement data can be expressed as a radar chart illustrated in FIG. 6. In the radar chart of FIG. 6, each piece of the measurement data is plotted as a point on an axis extending from a center to the nine apexes of a nonagon having nine apexes corresponding to the respective detectors 15, and the adjacent points are connected by straight lines. As described above, in a case in which the respective detectors 15 in the odor sensor 10 have the same configuration, the odor data can be referred to as a set of measurement data obtained by measuring adsorption characteristics of a certain odor substance (or a composition thereof) with respect to the substance adsorption membranes 13.

As illustrated in FIG. 1 to FIG. 3, the odor sensor 10 may be a card-like odor sensor chip that can be attached to and detached from the odor measurement apparatus 1.

For example, the sensor substrate 17 of the odor sensor 10 may be embedded in a card-like base material such that at least the substance adsorption membrane 13 is exposed to the outside of the base material. That is, in the perspective view of FIG. 1, a hole is formed in a surface of the odor sensor 10 facing the rear of the plane of the paper, and the odor sensor chip can be inserted into the hole. It is preferable that the sensor substrate 17 and the sensor surface 19 are disposed at positions which can be reached by the air introduced from the introduction port 33 in a state in which the odor sensor chip is inserted. By adopting such an odor sensor chip, the odor sensor 10 can be replaced. For example, the odor sensor 10 can be replaced with an odor sensor 10 having different substance adsorption membranes 13 or with an odor sensor 10 having the same set of substance adsorption membranes 13 but in a different arrangement.

<Imaging Device 20>

The imaging device 20 is a device which generates image data based on light emitted or reflected from an imaging target through the lens portion 21. The imaging device 20 is not particularly limited as long as the imaging device 20 can generate image data, and various types of cameras can be adopted. As illustrated in FIG. 1 to FIG. 3, the main body of the imaging device 20 is arranged inside the housing 30 of the odor measurement apparatus 1, and the lens portion 21 is exposed to the outside on the surface of the housing 30.

The lens portion 21 constitutes at least a part of an optical mechanism of the imaging device 20 and includes a lens. The lens portion 21 may include a lens barrel, protective glass, etc. in addition to the lens. The lens portion 21 on which light emitted or reflected from the imaging target is disposed on the predetermined surface 31 which is a surface of the odor measurement apparatus 1 on the side of the measurement target (imaging target).

<Control of Odor Measurement Apparatus>

Figure 7:
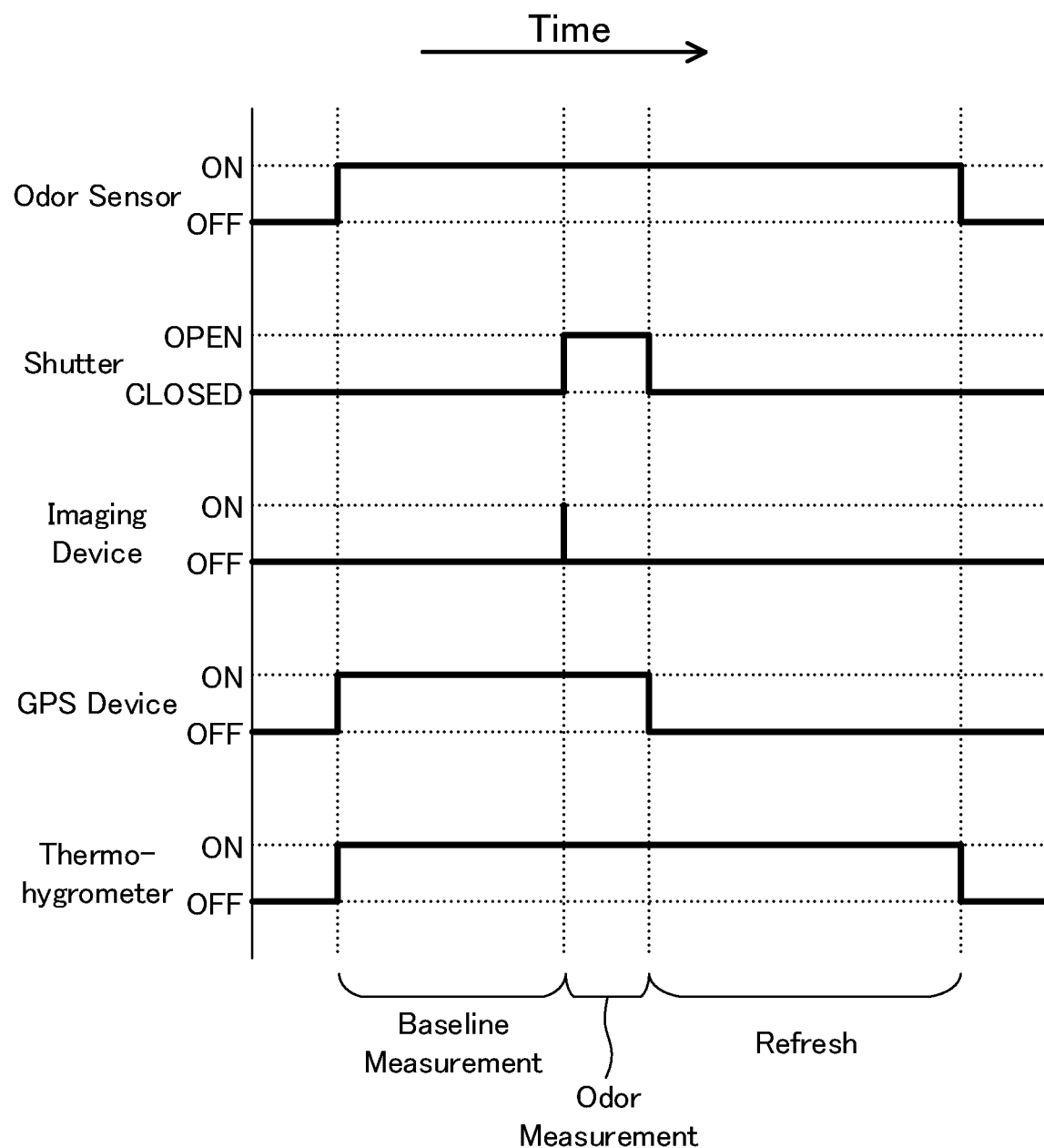
FIG. 7 is a timing chart for description of behavior control of various sensors.

Behavior of the above-described various sensors included in the odor measurement apparatus 1 can be controlled by an arithmetic processing device 61 executing a control program P2 stored in a storage device 62. Hereinafter, control of the behavior of the various sensors will be described with reference to FIG. 7. FIG. 7 is a timing chart for description of behavior control of the various sensors.

Here, a description will be given of the case of an odor measurement apparatus 1 in which the odor measurement apparatus 1 is incorporated in a portable information terminal, such as a smartphone or a tablet terminal. The control program P2 may be executed as an application executed by the arithmetic processing device 61 in the portable information terminal. It is presumed that the odor sensor 10, the imaging device 20, the GPS device 41, and the thermo-hygrometer 43 are included as the various sensors. Configurations of the respective devices, the sensors, etc. can be approximately set to the same configurations as those of the odor measurement apparatus 1 according to the first embodiment except that a display unit is arranged on a surface opposite to the predetermined surface 31 of the odor measurement apparatus 1 according to the first embodiment illustrated in FIG. 1 to FIG. 3.

When a user starts a control application executed based on the control program P1 and presses a measurement start button on an initial screen to start measurement, a standby screen is displayed on the display unit, then the odor sensor 10, the GPS device 41, and the thermo-hygrometer 43 are activated. Then, baseline measurement by the odor sensor 10, current position measurement by the GPS device 41, and measurement of air temperature and humidity by the thermo-hygrometer 43 are performed. When the baseline measurement, etc. is completed, a measurement button is displayed on the display unit. When the user presses the measurement start button, the imaging device 20 captures an image, the shutter 35 is opened to introduce air from the introduction port 33, and odor measurement by the odor sensor 10 is performed. After a lapse of a predetermined time, the shutter 35 is closed to end the odor measurement, and the current position measurement is ended in the GPS device 41. Thereafter, the standby screen is displayed on the display unit, and the odor sensor 10 is refreshed for a certain period of time. After a lapse of a predetermined time, the refreshing and the measurement of the air temperature and humidity by the thermo-hygrometer 43 are ended, and the initial screen is displayed on the display unit.

In the above-described control, the fan may be rotated at the time of introduction of air, and external air may be introduced toward the sensor surface 19. Further, at the time of baseline measurement and refreshing of the odor sensor 10, the fan may be reversely rotated to replace air near the sensor surface 19 with air introduced from the ventilation opening 37. Incidentally, in a case in which the fan is reversely rotated, it is preferable that the shutter 35 is kept open.

Second Embodiment

<Odor Data Management Apparatus 60>

As a second embodiment, a description will be given of an odor data management apparatus 60 which receives, stores, and manages the measurement data measured by the various sensors of the odor measurement apparatus 1 according to the first embodiment described above, with reference to drawings.

Figure 8:
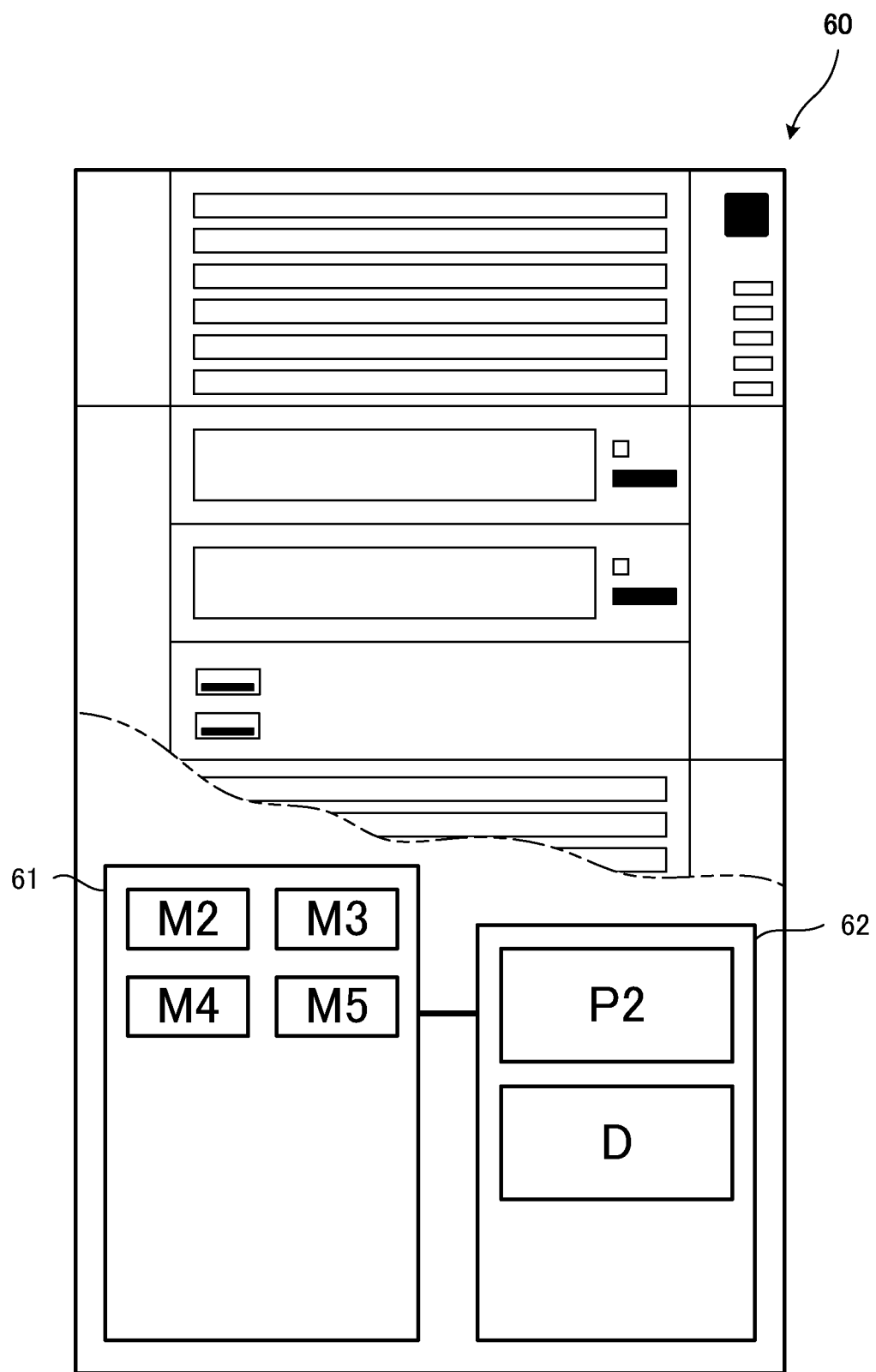
FIG. 8 is a partial cross-sectional view schematically illustrating an odor data management apparatus 60 according to the second embodiment.

FIG. 8 is a partial cross-sectional view schematically illustrating the odor data management apparatus 60 according to the second embodiment. The odor data management apparatus 60 has the arithmetic processing device 61 (CPU) and the storage device 62 (memory) therein. An odor data management program P2 and an odor data management database D are stored in the storage device 62. The odor data management program P2 causes the odor data management apparatus 60 to function as receiving means M2, storing means M3, extracting means M4, and returning means M5.

The receiving means has a function of receiving various data, such as the odor data and the image data, transmitted from the odor measurement apparatus 1 according to the first embodiment. Specific examples of the various data include odor data generated by the odor sensor 10, image data generated by the imaging device 20, latitude and longitude data generated by the GPS device 41, air temperature and humidity data generated by the thermo-hygrometer 43, air pressure data generated by the barometer 45, illuminance (light amount) data generated by the illuminometer 47, and date and time data. Incidentally, the receiving means may receive not only the various data transmitted from the odor measurement apparatus 1 but also various data copied to the odor data management apparatus 60 via various storage media, such as a universal serial bus (USB) memory, in which various data generated by the odor measurement apparatus 1 is stored.

The storing means has a function of storing various data received by the receiving means in association with each other in the odor data management database D. The odor data management database D is stored in the storage device 62 of the odor data management apparatus 60.

FIG. 9 is a database configuration diagram schematically illustrating the odor management database stored in the storage device 62 of the odor data management apparatus 60 according to the second embodiment. At least the odor data and the image data are stored in association with each other in the odor data management database D. In addition to the odor data and the image data, latitude and longitude data, air temperature and humidity data, air pressure data, illuminance (light amount) data, date and time data, etc. may be stored in association with each other.

In FIG. 9, the odor data, the image data, the date and time data, and the longitude and latitude data are stored in association with each other. Specifically, in FIG. 9, nine pieces of measurement data Ai to Aix measured by the respective sensor elements 11, date and time data A1, image data A2, longitude data A3, and latitude data A4 as attribute data of the odor data A are stored in association with each other. Likewise, odor data B and odor data C are stored in the odor data management database D in association with the measurement data and the attribute data.

The extracting means M4 has a function of extracting odor data approximate to specific odor data from a plurality of pieces of odor data stored in the odor data management database D by the storing means M3. That is, when an odor data of a certain odor (specific odor data) is included, odor data approximate thereto can be extracted from the odor data management database D.

That two sets of odor data are approximate to each other means that pieces of measurement data included in the odor data corresponding in the two sets of odor data are compared with each other, and a difference between values of the two compared pieces of measurement data is within a predetermined range. Here, the pieces of measurement data corresponding in the two sets of odor data are the pieces of measurement data by sensor elements 11 of the same kind among pieces of measurement data by the respective sensor elements 11 included in the odor data. That is, when determining whether two sets of odor data are approximate to each other, it is preferable to compare two sets of measurement data measured by sensor elements 11 having substance adsorption membranes 13 and detectors 15 of the same kind. Incidentally, when the two sets of measurement data to be compared which are measured by the sensor elements 11 including the same substance adsorption membranes 13 and detectors 15 are not used, two sets of measurement data to be compared which are measured by sensor elements 11 including substance adsorption membranes 13 having compositions close to each other and detectors 15 having the same configuration may be used. In addition, the predetermined range in a case in which the difference between the values of the measurement data is within the predetermined range can be arbitrarily determined for measurement data in each detector 15.

For example, in a case in which the odor data A and the odor data B are compared with each other, the measurement data Ai and the measurement data Bi measured by the same detector i can be compared with each other. Similarly, the measurement data Aii to Aix and the measurement data Bii to Bix can be compared with each other, respectively. Further, in measurement data in the respective sensor elements 11, in a case in which a difference between pieces of measurement data is within the predetermined range, it is possible to determine that the odor data A and the odor data B are approximate to each other. In a case in which the odor data A and the odor data C are compared with each other, the measurement data Ai and measurement data Ci measured by the same detector i can be compared with each other. Similarly, the measurement data Aii to Aix and measurement data Cii to Cix can be compared with each other, respectively. Further, in measurement data in the respective sensor elements 11, in a case in which any one difference between pieces of measurement data is out of the predetermined range, it can be determined that the odor data A and the odor data C are not approximate to each other.

The returning means M5 has a function of returning various data (hereinafter referred to as attribute data) other than odor data associated with odor data extracted by the extracting means M4 as a search result. Specific examples of the attribute data can include image data, latitude and longitude data, air temperature and humidity data, air pressure data, illuminance (light amount) data, date and time data, etc.

In a case of having odor data of a certain odor (specific odor data), attribute data associated with odor data approximate thereto is obtained from the odor data management database D as a search result by such extracting means M4 and returning means M5. Specifically, in a case in which the user acquires odor data of a favorite odor and searches for the acquired odor data using the odor data management apparatus 60, attribute data of odor data approximate to the favorite odor of the user is obtained as a search result. For example, in a case in which the user acquires odor data of a favorite perfume and conducts a search, as a search result thereof, attribute data acquired by another user using the odor measurement apparatus 1 is obtained as a search result. As such attribute data, it is possible to obtain attribute data, such as image data of a measurement target or latitude and longitude data of a measurement location obtained when another user has measured an odor approximate to the user's favorite perfume using the odor measurement apparatus 1. Examples of the image data in the case include a picture of a bottle or a package of the perfume, a store selling the perfume, etc. Therefore, by searching for odor data with regard to an odor of interest to the user, it is possible to obtain information about an odor approximate to the odor of interest to the user from information stored in the odor data management database D.

Third Embodiment

As a third embodiment, a description will be given of a robot mounting the odor measurement apparatus 1 according to the first embodiment. In the description below, the description analogous to that in the description of the above-described embodiments will be omitted.

The robot includes an introduction port 33 and an imaging device 20 on the predetermined surface 31 and measures an odor of air introduced from the introduction port 33 using the odor sensor 10. According to such a configuration, the robot can acquire odor data and image data of a measurement target.

The robot can store the measured odor data and image data in the storage device 62 in association with each other. The storage device may be mounted on the robot or may be mounted on a remote server communicably connected to the robot. In this way, it is possible to determine whether the measured odor data and image data of the measurement target are previously stored in the storage device. Further, in a case in which the same or similar odor data and image data are stored in the storage device, it is possible to determine that the measurement target has been previously measured. That is, in the case of the measurement target previously stored in the storage device, the robot can identify the measurement target. The robot can identify the measurement target not only by using the image data but also by combining the image data with the odor data.

For example, in a case in which the measurement target is a user (human) of the robot, it is possible to distinguish between the user and another person using image data and odor data measured regarding the user. Even in a case in which the face of the user may not be captured by the imaging device 20 of the robot, it is possible to improve identification accuracy of the user by combining image data with odor data.

As an example, in a pet type robot, in a case in which the introduction port 33 and the imaging device 20 are mounted on the face portion thereof, the pet type robot can identify the user based on image data and odor data of the user. The pet type robot can be operated so that when the user moves, the robot follows thereafter.

REFERENCE SIGNS LIST

1: odor measurement apparatus
10: odor sensor
11: sensor element
13: substance adsorption membrane
15: detector
17: sensor substrate
19: sensor surface
20: imaging device
21: lens portion
30: housing
31: predetermined surface
33: introduction port
34: guide portion
35: shutter
37: ventilation opening
41: GPS device
43: thermo-hygrometer
44: measuring portion
45: barometer
47: illuminometer
48: measuring portion
49: communication device
51: arithmetic processing device
52: storage device
60: odor data management apparatus
61: arithmetic processing device
62: storage device
D: odor data management database
M1: odor acquiring means
M2: receiving means
M3: storing means
M4: extracting means
M5: returning means
P1: control program
P2: odor data management program

What is claimed is:

1. An odor measurement apparatus comprising:
an odor sensor detecting an odor;
an imaging device having a lens portion;
a housing comprising the odor sensor and the imaging device therein;
an arithmetic processing device controlling the behavior of the odor sensor and the imaging device by executing a control program,
wherein an imaging direction of the imaging device and an introduction direction of air when the air is guided to a sensor surface of the odor sensor through an introduction port, which is disposed on the housing, are substantially the same direction,
wherein an opening/closing device capable of opening and closing the introduction port is arranged in the odor measurement apparatus,
wherein the odor sensor is a removable odor sensor chip that can be attached to, and detached from, the odor measurement apparatus through a hole formed on the housing,
wherein, when a measurement start button is pressed while the control program is executed, a baseline measurement by the odor sensor is performed based on the behavior control provided by the arithmetic processing device, and
wherein, when the measurement start button is pressed after the baseline measurement is completed, image capture by the imaging device accompanied by opening of a shutter by the opening/closing device, and odor measurement by the odor sensor, are performed based on the behavior control provided by the arithmetic processing device.

2. The odor measurement apparatus according to claim 1, wherein the odor sensor includes a plurality of sensor elements, each having a substance adsorption membrane which adsorbs odor substances in air and a detector which detects an adsorption state of the odor substances to the substance adsorption membrane, and
wherein an adsorption characteristic of the odor substances to the substance adsorption membrane is different for each of the plurality of sensor elements.

3. The odor measurement apparatus according to claim 2, wherein the lens portion of the imaging device and the introduction port are disposed on a predetermined surface corresponding to a surface on the same side in the housing.

4. The odor measurement apparatus according to claim 3, wherein a ventilation opening is formed on another surface different from the predetermined surface in the housing.

5. The odor measurement apparatus according to claim 1, wherein the lens portion of the imaging device and the introduction port are disposed on a predetermined surface corresponding to a surface on the same side in the housing.

6. The odor measurement apparatus according to claim 5, wherein a ventilation opening is formed on another surface different from the predetermined surface in the housing.

7. The odor measurement apparatus according to claim 1, further comprising:
a fan controlling introduction of air from the introduction port to the sensor surface.

8. The odor measurement apparatus according to claim 1, further comprising:
an attribute data acquisition device including at least one selected from a group consisting of a global positioning system (GPS) device, a thermo-hygrometer, a barometer, and an illuminometer.

9. The odor measurement apparatus according to claim 1, further comprising:
a communication device transmitting odor data measured by the odor sensor and image data generated by the imaging device.

10. An odor data management apparatus comprising:
a receiver receiving the odor data and the image data transmitted from the odor measurement apparatus according to claim 9; and
storage storing the received odor data and image data in association with each other.

11. The odor data management apparatus according to claim 10, further comprising:
an extractor extracting odor data approximate to specific odor data from a plurality of sets of odor data stored in the storage; and
a returner returning image data associated with odor data extracted by the extractor as a search result.

* * * * *